United States Patent
Pigamo et al.

(10) Patent No.: US 11,459,285 B2
(45) Date of Patent: Oct. 4, 2022

(54) PROCESS FOR MANUFACTURING TETRAFLUOROPROPENE

(71) Applicant: Arkema France, Colombes (FR)

(72) Inventors: Anne Pigamo, Francheville (FR); Laurent Wendlinger, Soucieu en Jarrest (FR); Dominique Duer-Bert, Charly (FR)

(73) Assignee: ARKEMA FRANCE, Colombes (FR)

( * ) Notice: Subject to any disclaimer, the term of this patent is extended or adjusted under 35 U.S.C. 154(b) by 0 days.

(21) Appl. No.: 16/250,141

(22) Filed: Jan. 17, 2019

(65) Prior Publication Data

US 2019/0152883 A1   May 23, 2019

Related U.S. Application Data

(62) Division of application No. 15/321,462, filed as application No. PCT/FR2015/051653 on Jun. 22, 2015, now Pat. No. 10,227,275.

(30) Foreign Application Priority Data

Jul. 2, 2014 (FR) ...................................... 1456303

(51) Int. Cl.
   *C07C 17/20* (2006.01)
   *B01J 12/00* (2006.01)
   *C07C 21/18* (2006.01)

(52) U.S. Cl.
   CPC ........... *C07C 17/206* (2013.01); *B01J 12/007* (2013.01); *C07C 21/18* (2013.01);
   (Continued)

(58) Field of Classification Search
   CPC ....... C07C 17/206; C07C 21/18; C07C 17/20; B01J 12/007; B01J 2219/0004; B01J 2219/00038; Y02P 20/582; Y02P 20/584
   (Continued)

(56) References Cited

U.S. PATENT DOCUMENTS 2,773,014 A * 12/1956 Snuggs .................... B01J 38/12
                                                            208/65
4,902,838 A    2/1990 Manzer et al.
(Continued)

FOREIGN PATENT DOCUMENTS

EP          0 449 617          10/1991
EP          0449617 A2 *       10/1991      ........... C07C 17/206
(Continued)

OTHER PUBLICATIONS

International Search Report (PCT/ISA/210) dated Sep. 1, 2015, by the French Patent Office as the International Searching Authority for International Application No. PCT/FR2015/051653.
(Continued)

*Primary Examiner* — Huy Tram Nguyen
(74) *Attorney, Agent, or Firm* — Buchanan Ingersoll & Rooney P.C.

(57) ABSTRACT

A process for manufacturing tetrafluoropropene, including, alternately: at least one step of reacting a chlorinated compound with hydrofluoric acid in the gas phase, in the presence of a fluorination catalyst, the proportion of oxygen optionally present being less than 0.05 mol. % relative to the chlorinated compound; a step of regenerating the fluorination catalyst by bringing the fluorination catalyst into contact with a regeneration stream including an oxidizing agent. Also, equipment suitable for carrying out this process.

19 Claims, 6 Drawing Sheets

(52) U.S. Cl.
CPC ............... B01J 2219/0004 (2013.01); B01J 2219/00038 (2013.01); Y02P 20/582 (2015.11); Y02P 20/584 (2015.11)

(58) Field of Classification Search
USPC ........................................................ 422/600
See application file for complete search history.

(56) References Cited

U.S. PATENT DOCUMENTS

| | | | | |
|---|---|---|---|---|
| 5,227,350 | A * | 7/1993 | Scott | B01J 23/90 502/36 |
| 5,322,597 | A | 6/1994 | Childs et al. | |
| 5,334,784 | A * | 8/1994 | Blake | B01D 53/68 570/165 |
| 5,919,728 | A * | 7/1999 | Rinaldi | C07C 17/21 502/305 |
| 8,614,361 | B2 | 12/2013 | Suzuki et al. | |
| 8,618,338 | B2 | 12/2013 | Elsheikh et al. | |
| 9,255,045 | B2 | 2/2016 | Pigamo et al. | |
| 9,340,473 | B2 * | 5/2016 | Pigamo | B01J 23/866 |
| 9,708,234 | B2 * | 7/2017 | Chaki | C07C 17/206 |
| 9,834,499 | B2 | 12/2017 | Pigamo et al. | |
| 10,227,275 | B2 | 3/2019 | Pigamo et al. | |
| 10,427,998 | B2 | 10/2019 | Pigamo et al. | |
| 10,532,965 | B2 | 1/2020 | Pigamo et al. | |
| 11,028,027 | B2 | 6/2021 | Wendlinger et al. | |
| 11,034,635 | B2 | 6/2021 | Wendlinger et al. | |
| 11,084,768 | B2 | 8/2021 | Wendlinger et al. | |
| 11,242,304 | B2 | 2/2022 | Pigamo et al. | |
| 2004/0015022 | A1* | 1/2004 | Ohno | C07C 17/10 570/164 |
| 2009/0240090 | A1 | 9/2009 | Merkel et al. | |
| 2009/0287026 | A1 | 11/2009 | Kopkalli et al. | |
| 2010/0191025 | A1 | 7/2010 | Perdrieux | |
| 2011/0031436 | A1 | 2/2011 | Mahler et al. | |
| 2013/0197281 | A1 | 8/2013 | Hintzer et al. | |
| 2013/0267740 | A1 | 10/2013 | Wendlinger et al. | |
| 2014/0012051 | A1 | 1/2014 | Pigamo et al. | |
| 2014/0039228 | A1 | 2/2014 | Pigamo et al. | |
| 2014/0275653 | A1 | 9/2014 | Pigamo et al. | |
| 2015/0008357 | A1 | 1/2015 | Furuta et al. | |
| 2015/0197467 | A1 | 7/2015 | Pigamo et al. | |
| 2015/0203422 | A1 | 7/2015 | Deur-Bert et al. | |
| 2016/0115104 | A1 | 4/2016 | Pigamo et al. | |
| 2016/0237009 | A1 | 8/2016 | Deur-Bert et al. | |
| 2017/0158586 | A1 | 6/2017 | Collier et al. | |
| 2017/0210686 | A1 | 7/2017 | Pigamo | |
| 2018/0093934 | A1 | 4/2018 | Pigamo et al. | |
| 2018/0148394 | A1 | 5/2018 | Pigamo et al. | |
| 2019/0127303 | A1 | 5/2019 | Ondrus et al. | |
| 2019/0375698 | A1 | 12/2019 | Pigamo et al. | |
| 2020/0407293 | A1 | 12/2020 | Wendlinger et al. | |
| 2021/0002188 | A1 | 1/2021 | Wendlinger et al. | |
| 2021/0002189 | A1 | 1/2021 | Wendlinger et al. | |
| 2021/0238112 | A1 | 8/2021 | Pigamo et al. | |
| 2021/0261485 | A1 | 8/2021 | Hisler et al. | |
| 2021/0340083 | A1 | 11/2021 | Boutier et al. | |

FOREIGN PATENT DOCUMENTS

| | | |
|---|---|---|
| EP | 0 582 192 A1 | 2/1994 |
| EP | 0 939 071 A1 | 9/1999 |
| FR | 3 013 606 | 5/2015 |
| JP | WO2013/154059 A1 | 10/2013 |
| WO | WO 01/81353 A1 | 11/2001 |
| WO | WO 2007/079431 A2 | 7/2007 |
| WO | WO 2008/040969 A2 | 4/2008 |
| WO | WO 2008/054781 A1 | 5/2008 |
| WO | WO 2008/149011 A2 | 12/2008 |
| WO | WO 2009/118628 A1 | 10/2009 |
| WO | WO 2009/137658 A2 | 11/2009 |
| WO | WO 2011/077192 A1 | 6/2011 |
| WO | WO 2012/012113 A1 | 1/2012 |
| WO | WO 2012/052797 A1 | 4/2012 |
| WO | WO 2012/098421 A1 | 7/2012 |
| WO | WO 2012/098422 A1 | 7/2012 |
| WO | WO 2013/088195 A1 | 6/2013 |
| WO | WO 2013/182816 A1 | 12/2013 |
| WO | WO 2014/010750 A1 | 1/2014 |
| WO | WO 2017/178857 A1 | 10/2017 |

OTHER PUBLICATIONS

U.S. Appl. No. 16/545,294, Anne Pigamo and Bertrand Collier, filed Aug. 20, 2019.
Pigamo, Anne, et al., U.S. Appl. No. 17/053,250, entitled "Method for Producing 1-Chloro-3,3,3-Trifluoropropene," filed in the U.S. Patent and Trademark Office on Nov. 5, 2020.
Hisler, Kevin, et al., U.S. Appl. No. 17/251,328, entitled "Method for Producing 1-Chloro-3,3,3-Trifluoropropene," filed in the U.S. Patent and Trademark Office on Dec. 11, 2020.
Boutier, Jean-Christophe, et al., U.S. Appl. No. 17/280,547, entitled "Stabilization of 1-Chloro-3,3,3-Trifluoropropene," filed in the U.S. Patent and Trademark Office on Mar. 26, 2021.
International Search Report (PCT/ISA/210) and Written Opinion (PCT/ISA/237), issued in PCT/FR2019/050477, dated Jun. 19, 2019, European Patent Office, Rijswijk, NL, 22 pages.
International Search Report (PCT/ISA/210) and Written Opinion (PCT/ISA/237), issued in PCT/FR2019/050478, dated Jun. 26, 2019, European Patent Office, Rijswijk, NL, 16 pages.
International Search Report (PCT/ISA/210) and Written Opinion (PCT/ISA/237), issued in PCT/FR2019/050479, dated Jun. 6, 2019, European Patent Office, Rijswijk, NL, 18 pages.
Bonnet, Philippe, "Liquid-phase HF Fluorination," *Multiphase Homogeneous Catalysis*, vol. 2, Chapter 5 "Catalysis in Nonaqueous Ionic Liquids (ILs)", 5.2 State of the Art, (2002), pp. 535-542, 2002, Wiley-VCH Verlag GmbH & Co. KGaA, Weinheim, DE.
Mukerjee, Pasupati, et al., "Effect of Temperature on the Electrical Conductivity and the Thermodynamics of Micelle Formation of Sodium Perfluorooctanoate," *Journal of Physical Chemistry*, Nov. 1, 1985, pp. 5308-5312, vol. 89, No. 24, American Chemical Society, US (XP055519639).
Wendlinger, Laurent, et al., U.S. Appl. No. 16/976,819, entitled "Process for the Production of 2,3,3,3-Tetrafluoropropene,"filed in the U.S. Patent and Trademark Office on Aug. 31, 2020.
Wendlinger, Laurent, et al., U.S. Appl. No. 16/976,520, entitled "Process for Producing 2-Chloro-3,3,3-Trifluoropropene," filed in the U.S. Patent and Trademark Office on Aug. 28, 2020.
Wendlinger, Laurent, et al., U.S. Appl. No. 16/976,599, entitled "Process for the Production of 2,3,3,3-Tetrafluoropropene," filed in the U.S. Patent and Trademark Office on Aug. 28, 2020.
Pigamo, Anne, et al., U.S. Appl. No. 17/557,668 entitled "Method for Producing 1-Chloro-3,3,3-Trifluoropropene," filed in the U.S. Patent and Trademark Office Dec. 21, 2021.

* cited by examiner

PROCESS FOR MANUFACTURING TETRAFLUOROPROPENE

CROSS REFERENCE TO RELATED APPLICATIONS

The present application is a divisional of U.S. application Ser. No. 15/321,462, filed on Dec. 22, 2016, which is a U.S. national stage of International Application No. PCT/FR2015/051653, filed on Jun. 22, 2015, which claims the benefit of French Application No. 1456303, filed on Jul. 2, 2014. The entire contents of each of U.S. application Ser. No. 15/321,462, International Application No. PCT/FR2015/051653, and French Application No. 1456303 are hereby incorporated herein by reference in their entirety.

TECHNICAL FIELD

The present invention relates to a process for the manufacture of tetrafluoropropene (HFO-1234) and in particular of 2,3,3,3-tetrafluoropropene (HFO-1234yf), and also to a plant suitable for the implementation of this process.

TECHNICAL BACKGROUND

Greenhouse gases are gaseous components which absorb the infrared radiation emitted by the surface of the earth, thus contributing to the greenhouse effect. The increase in their concentration in the atmosphere is one of the factors causing global warming.

The production of the chlorofluorocarbons (CFCs) and hydrochlorofluorocarbons (HCFCs) used in refrigeration and air conditioning systems has thus been successively regulated by the Montreal protocol and then the Kyoto protocol. There exists a need to develop new molecules which are as effective and which in particular exhibit the smallest possible global warming potential. This is the case with hydrofluoroolefins and in particular HFO-1234yf, which is a particularly useful compound.

It is known to produce hydrofluoroolefins or hydrofluorocarbons by fluorination of hydrochloroolefins or of hydrochlorocarbons in particular. This fluorination is generally a catalytic fluorination using hydrofluoric acid as fluorinating agent.

The fluorination reaction generally has to be carried out at a high temperature (more than 300° C.) in the gas phase, in the presence of a supported or bulk solid catalyst.

It is known to provide cofeeding with an oxidizing agent, in particular air, or optionally chlorine, in order to preserve the lifetime of the catalyst and to limit the deposition of coke at its surface during the reaction stage.

The document U.S. Pat. No. 8,614,361 describes a process for the manufacture of HFO-1234yf by reacting HCFO-1233xf with HF in the presence of a high oxygen content.

The document U.S. Pat. No. 8,618,338 describes a process for the manufacture of fluoroolefin in two stages, in particular a first stage of reaction in the liquid phase starting from 1,1,2,3-tetrachloropropene (HCO-1230xa), in order to obtain the intermediate HCFO-1233xf, and a second stage of reaction in the gas phase starting from HCFO-1233xf, in order to obtain HFO-1234yf.

The document WO 2013/088195 teaches a process for the manufacture of HFO-1234yf in two stages, a first stage of fluorination in the gas phase of 1,1,1,2,3-pentachloropropane (HCC-240db) and/or of 1,1,2,2,3-pentachloropropane (HCC-240aa), in order to obtain the intermediate HCFO-1233xf, and then a second stage of reaction in the gas phase starting from HCFO-1233xf, in order to obtain HFO-1234yf.

The documents WO 2012/098421 and WO 2012/098422 teach the activation and the regeneration of fluorination catalysts.

The document WO 2013/182816 describes a chemical reaction process for the alternating implementation of a phase of catalytic reaction and of a phase of regeneration of catalyst in a reactor.

There still exists a need to improve the processes for the manufacture of HFO-1234 compounds, such as HFO-1234yf, and in particular to produce these compounds with a high yield and with a high degree of purity.

SUMMARY

The invention relates first to a process for the manufacture of tetrafluoropropene, comprising, alternately:
- at least one stage of reaction of a chlorinated compound with hydrofluoric acid in the gas phase, in the presence of a fluorination catalyst, the proportion of oxygen optionally present being less than 0.05 mol % with respect to the chlorinated compound;
- a stage of regeneration of the fluorination catalyst by bringing the fluorination catalyst into contact with a regeneration stream comprising an oxidizing agent.

According to one embodiment, the stage of reaction of the chlorinated compound with hydrofluoric acid is carried out essentially in the absence of oxygen and preferably essentially in the absence of any oxidizing agent.

According to one embodiment, the regeneration stream contains at least 1 mol % of oxygen with respect to the total regeneration stream.

According to one embodiment, the stage of reaction of the chlorinated compound with hydrofluoric acid is carried out in a single reactor, separately in time with respect to the stage of regeneration of the fluorination catalyst.

According to one embodiment, the stage of reaction of the chlorinated compound with hydrofluoric acid is carried out in at least one first reactor, simultaneously with the implementation of the stage of regeneration of the fluorination catalyst in at least one second reactor.

According to one embodiment, the tetrafluoropropene is 2,3,3,3-tetrafluoropropene.

According to one embodiment, the tetrafluoropropene is 1,3,3,3-tetrafluoropropene.

According to one embodiment, the chlorinated compound is chosen from tetrachloropropenes, chlorotrifluoropropenes, pentachloropropanes and mixtures of these.

According to one embodiment, the chlorinated compound is 2-chloro-3,3,3-trifluoropropene and the tetrafluoropropene is 2,3,3,3-tetrafluoropropene.

According to one embodiment, the chlorinated compound is 1,1,1,2,3-pentachloropropane and/or 1,1,2,2,3-pentachloropropane and the tetrafluoropropene is 2,3,3,3-tetrafluoropropene.

According to one embodiment, the chlorinated compound is 1-chloro-3,3,3-trifluoropropene and the tetrafluoropropene is 1,3,3,3-tetrafluoropropene.

According to one embodiment, the process comprises:
- a preliminary stage of manufacture of the chlorinated compound, which is preferably a preliminary stage of reaction of a preliminary compound with hydrofluoric acid in the gas phase, in the presence of a preliminary fluorination catalyst, the proportion of oxygen optionally present being less than 0.05 mol % with respect to the preliminary compound.

According to one embodiment, the preliminary stage of reaction is carried out alternately with:
- a stage of regeneration of the preliminary fluorination catalyst by bringing the preliminary fluorination catalyst into contact with a regeneration stream comprising an oxidizing agent.

According to one embodiment, the preliminary compound is 1,1,1,2,3-pentachloropropane and/or 1,1,2,2,3-pentachloropropane, the chlorinated compound is 1-chloro -3,3,3-trifluoropropene and the tetrafluoropropene is 2,3,3,3-tetrafluoropropene.

According to one embodiment, the process comprises:
- the collecting of a stream of products on conclusion of the preliminary reaction stage;
- the separation of the stream of products into a first stream comprising hydrochloric acid and tetrafluoropropene and a second stream comprising hydrofluoric acid and the chlorinated compound;
- the use of said second stream to carry out the stage of reaction of the chlorinated compound with hydrofluoric acid; and
- optionally, the collecting of a stream of products on conclusion of the stage of reaction of the chlorinated compound with hydrofluoric acid and the recycling of the latter in the preliminary reaction stage.

The invention also relates to a plant for the manufacture of tetrafluoropropene, comprising at least one gas-phase fluorination reactor comprising a bed of fluorination catalyst, said gas-phase fluorination reactor being configured in order to be fed alternately by:
- a system for feeding with reaction stream comprising a chlorinated compound and hydrofluoric acid, the proportion of oxygen optionally present in this reaction stream being less than 0.05 mol % with respect to the chlorinated compound; and
- a system for feeding with regeneration stream comprising an oxidizing agent.

According to one embodiment, the reaction stream is essentially devoid of oxygen and preferably of any oxidizing agent.

According to one embodiment, the regeneration stream contains at least 1 mol % of oxygen with respect to the total regeneration stream.

According to one embodiment, the plant comprises a single reactor configured in order to be fed alternately by the system for feeding with reaction stream and the system for feeding with regeneration stream.

According to one embodiment, the plant comprises a plurality of reactors, each being configured in order to be fed alternately by a system for feeding with reaction stream and a system for feeding with regeneration stream.

According to one embodiment, the plant is configured so that, when a reactor is fed by the system for feeding with reaction stream, another reactor is fed by the system for feeding with regeneration stream.

According to one embodiment, the plant is configured so that:
- the system for feeding with reaction stream feeds the reactor at the bottom and the system for feeding with regeneration stream feeds the reactor at the bottom; or
- the system for feeding with reaction stream feeds the reactor at the bottom and the system for feeding with regeneration stream feeds the reactor at the top; or
- the system for feeding with reaction stream feeds the reactor at the top and the system for feeding with regeneration stream feeds the reactor at the bottom; or
- the system for feeding with reaction stream feeds the reactor at the top and the system for feeding with regeneration stream feeds the reactor at the top.

According to one embodiment:
- the tetrafluoropropene is 2,3,3,3-tetrafluoropropene; or
- the tetrafluoropropene is 1,3,3,3-tetrafluoropropene.

According to one embodiment, the chlorinated compound is chosen from tetrachloropropenes, chlorotrifluoropropenes, pentachloropropanes and mixtures of these; and preferably:
- the chlorinated compound is 2-chloro-3,3,3-trifluoropropene and the tetrafluoropropene is 2,3,3,3-tetrafluoropropene; or
- the chlorinated compound is 1,1,1,2,3-pentachloropropane and/or 1,1,2,2,3-pentachloropropane and the tetrafluoropropene is 2,3,3,3-tetrafluoropropene; or
- the chlorinated compound is 1-chloro-3,3,3-trifluoropropene and the tetrafluoropropene is 1,3,3,3-tetrafluoropropene.

According to one embodiment, the plant comprises:
- at least one unit for the manufacture of chlorinated compound, which preferably is at least one preliminary fluorination reactor; configured in order to be fed by:
- a system for feeding with reaction medium comprising a preliminary compound and hydrofluoric acid, the proportion of oxygen optionally present in this reaction stream being less than 0.05 mol % with respect to the preliminary compound.

According to one embodiment, the preliminary fluorination reactor is also configured in order to be fed by a system for feeding with regeneration stream comprising an oxidizing agent.

According to one embodiment, the preliminary compound is 1,1,1,2,3-pentachloropropane and/or 1,1,2,2,3-pentachloropropane, the chlorinated compound is 1-chloro -3,3,3-trifluoropropene and the tetrafluoropropene is 2,3,3,3-tetrafluoropropene.

According to one embodiment, the plant comprises:
- at least one first catalytic fluorination reactor;
- at least one second catalytic fluorination reactor;
- a system for collecting a stream of products connected at the outlet of the first catalytic fluorination reactor;
- a separation unit fed by the system for collecting a stream of products;
- a first collecting pipe and a second collecting pipe which are connected at the outlet of the separation unit, the first collecting pipe being configured in order to transport a stream comprising hydrochloric acid and tetrafluoropropene and the second collecting pipe being configured in order to transport a stream comprising hydrofluoric acid and chlorinated compound;
- an intermediate collecting system connected at the outlet of the second reactor;
- a first system for feeding with reaction medium configured in order to feed the first reactor, this being itself fed by the intermediate collecting system;
- a second system for feeding with reaction medium configured in order to feed the second reactor, this being itself fed by the second collecting pipe;
- a system for feeding with regeneration stream configured in order to feed the first reactor and/or the second reactor; and
- a system for collecting a stream of gases resulting from the regeneration.

According to one embodiment, the plant comprises at least two second reactors configured so that, when one of these reactors is fed by the second system for feeding with reaction stream, the other reactor is fed by the system for feeding with regeneration stream.

According to one embodiment, the plant comprises at least two first reactors and two second reactors configured so that, when one of the first reactors and one of the second reactors are respectively fed by the first system for feeding with reaction stream and the second system for feeding with reaction stream, the other first reactor and the other second reactor are fed by the system for feeding with regeneration stream; and which, preferably, is configured so that one and the same regeneration stream resulting from the system for feeding with regeneration stream passes successively into the first reactor and then the second reactor or passes successively into the second reactor and then the first reactor.

According to one embodiment, the plant comprises a single second reactor configured in order to be fed sequentially either by the second system for feeding with reaction stream or by the system for feeding with regeneration stream.

According to one embodiment, the plant comprises a single first reactor and a single second reactor configured in order to be fed sequentially either by the second system for feeding with reaction stream or by the system for feeding with regeneration stream; and which, preferably, is configured so that one and the same regeneration stream resulting from the system for feeding with regeneration stream passes successively into the first reactor and then the second reactor or passes successively into the second reactor and then the first reactor.

The invention also relates to a composition comprising tetrafluoropropene and containing, in molar proportions:
less than 100 ppm of chloromethane; and/or
less than 100 ppm of 1,1-difluoroethane; and/or
less than 100 ppm of fluoromethane; and/or
less than 100 ppm of difluoromethane.

According to one embodiment, the tetrafluoropropene is 2,3,3,3-tetrafluoropropene.

According to one embodiment, the composition contains, in molar proportions:
less than 50 ppm of chloromethane; and/or
less than 50 ppm of 1,1-difluoroethane; and/or
less than 50 ppm of fluoromethane; and/or
less than 50 ppm of difluoromethane.

The present invention makes it possible to overcome the disadvantages of the state of the art. It more particularly provides a process for the manufacture of HFO-1234 (and in particular of HFO-1234yf) which has a high yield and which provides the desired product in a high degree of purity.

This is accomplished by virtue of the discovery, by the present inventors, that some fluorination reaction stages can be carried out essentially in the absence of oxidizing agent, such as oxygen, without the lifetime of the fluorination catalyst being visibly affected over a predetermined period, so long as intermediate regeneration stages are provided.

An advantage resulting therefrom is that a gaseous stream of HFO-1234 of a higher purity is obtained as it is obtained essentially in the absence of oxygen during the reaction. The content of carbon oxides and also of compounds containing one or two carbons is markedly reduced with respect to the state of the art. The downstream treatment and the final purification of the desired product are thus simplified, guaranteeing that the final product is obtained preferably with a purity of greater than or equal to 98%, advantageously of greater than or equal to 99% and very advantageously of greater than or equal to 99.8% by weight. The hydrochloric acid coproduced is also more easily recovered in value.

DETAILED DESCRIPTION OF EMBODIMENTS

Figure 1A:
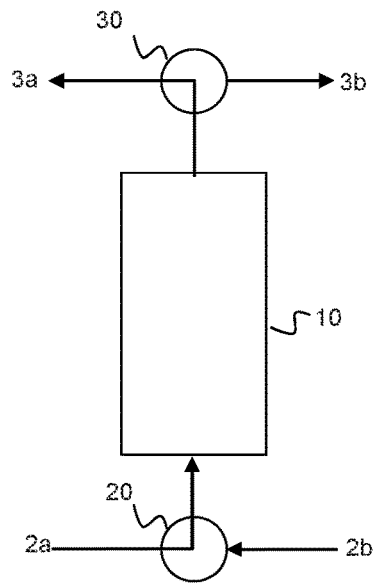
FIGS. 1a and 1b diagrammatically represent an embodiment of a plant according to the invention with just one catalytic fluorination reactor, in two different operating configurations.

The invention is now described in more detail and without limitation in the description which follows.

Unless otherwise mentioned, the percentages and proportions shown are values by weight.

The invention provides for the production of HFO-1234 by catalytic gas-phase fluorination; this catalytic fluorination is, according to the invention, alternated with the regeneration of the fluorination catalyst. In some embodiments, the invention provides for the production of HFO-1234 in several fluorination stages.

Fluorination Reaction for the Production of HFO-1234

The invention provides at least one fluorination stage, making it possible to produce HFO-1234 from a chlorinated compound.

The HFO-1234 can in particular be HFO-1234yf or else HFO-1234ze (1,3,3,3-tetrafluoropropene), in the cis or trans form or in the form of a mixture of cis and trans forms.

"Chlorinated compound" is understood to mean an organic compound comprising one or more chlorine atoms. This compound preferably comprises three carbon atoms.

This chlorinated compound is preferably a propane or a propene having substituents chosen from F, Cl, I and Br (preferably from F and Cl) and comprising at least one Cl substituent.

It is understood that "chlorinated compound" is also understood to mean mixtures of compounds.

Preferably, the chlorinated compound is a tetrachloropropene, a chlorotrifluoropropene, a pentachloropropane or a mixture of these.

In one embodiment, the chlorinated compound is 2-chloro-3,3,3-trifluoropropene (HCFO-1233xf), in order to produce HFO-1234yf.

In another embodiment, the chlorinated compound is 1-chloro-3,3,3-trifluoropropene (HCFO-1233zd), in order to produce HFO-1234ze.

In another embodiment, the chlorinated compound is 1,1,1,2,3-pentachloropropane (HCC-240db) or 1,1,2,2,3- pentachloropropane (HCC-240aa), or a mixture of the two, in order to produce HFO-1234yf.

According to yet another embodiment, the chlorinated compound is 2,3-dichloro-1,1,1-trifluoropropane (HCFC-243db), in order to produce HFO-1234yf.

According to yet another embodiment, the chlorinated compound is 1,1,2,3-tetrachloropropene (HCO-1230xa) or 2,3,3,3-tetrachloropropene (HCO-1230xf) or a mixture of these two compounds, in order to produce HFO-1234yf.

The conversion of the chlorinated compound to give HFO-1234 can be a direct conversion or an indirect conversion (that is to say, involving an intermediate product).

The fluorination of the chlorinated compound to give HFO-1234 is carried out in one or more gas-phase fluorination reactors comprising a bed of fluorination catalyst.

The catalyst used can, for example, be based on a metal comprising a transition metal oxide or a derivative or a halide or an oxyhalide of such a metal. Mention may be made, for example, of $FeCl_3$, chromium oxyfluoride, chromium oxides (optionally subjected to fluorination treatments), chromium fluorides and their mixtures. Other possible catalysts are catalysts supported on carbon, catalysts based on antimony or catalysts based on aluminum (for example $AlF_3$ and $Al_2O_3$, alumina oxyfluoride and alumina fluoride).

Use may be made, in general, of a chromium oxyfluoride, an aluminum fluoride, an aluminum oxyfluoride or a supported or unsupported catalyst containing a metal, such as Cr, Ni, Fe, Zn, Ti, V, Zr, Mo, Ge, Sn, Pb, Mg or Sb.

Reference may be made, in this regard, to the document WO 2007/079431 (on p. 7, l. 1-5 and 28-32), to the document EP 939071 (section [0022]), to the document WO 2008/054781 (on p. 9, l. 22-p. 10, l. 34) and to the document WO 2008/040969 (claim 1), to which documents reference is expressly made.

The catalyst is more particularly preferably based on chromium and it is more particularly a mixed catalyst comprising chromium.

According to one embodiment, a mixed catalyst comprising chromium and nickel is used. The Cr/Ni molar ratio (on the basis of the metal element) is generally from 0.5 to 5, for example from 0.7 to 2, for example approximately 1. The catalyst can contain from 0.5 to 20% by weight of chromium and from 0.5 to 20% by weight of nickel, preferably from 2 to 10% of each.

The metal can be present in the metallic form or in the form of a derivative, for example an oxide, halide or oxyhalide. These derivatives are preferably obtained by activation of the catalytic metal.

The support preferably consists of aluminum, for example alumina, activated alumina or aluminum derivatives, such as aluminum halides and aluminum oxyhalides, for example described in the document U.S. Pat. No. 4,902,838 or obtained by the activation process described above.

The catalyst can comprise chromium and nickel in an activated or nonactivated form, on a support which has or has not been subjected to activation.

Reference may be made to the document WO 2009/118628 (in particular on p. 4, l. 30-p. 7, l. 16), to which reference is expressly made here.

Another preferred embodiment is based on a mixed catalyst containing chromium and at least one element chosen from Mg and Zn. The Mg or Zn/Cr atomic ratio is preferably from 0.01 to 5.

Before its use, the catalyst is preferably subjected to activation with air, oxygen or chlorine and/or with HF.

For example, the catalyst is preferably subjected to activation with air or oxygen and HF at a temperature of 100 to 500° C., preferably of 250 to 500° C. and more particularly of 300 to 400° C. The activation time is preferably from 1 to 200 h and more particularly from 1 to 50 h.

This activation can be followed by a stage of final fluorination activation in the presence of an oxidizing agent, of HF and of organic compounds.

The HF/organic compounds molar ratio is preferably from 2 to 40 and the oxidizing agent/organic compounds molar ratio is preferably from 0.04 to 25. The temperature of the final activation is preferably from 300 to 400° C. and its duration is preferably from 6 to 100 h.

The gas-phase fluorination reaction can be carried out:
  with an HF/chlorinated compound molar ratio of 1:1 to 150:1, preferably of 3:1 to 100:1 and more particularly preferably of 5:1 to 50:1;
  with a contact time of 1 to 100 s, preferably 1 to 50 s and more particularly 2 to 40 s (catalyst volume divided by the total incoming stream, adjusted to the operating temperature and pressure);
  at an absolute pressure ranging from 0.1 to 50 bar, preferably from 0.3 to 15 bar;
  at a temperature (temperature of the catalyst bed) of 100 to 500° C., preferably of 200 to 450° C. and more particularly of 250 to 400° C.

The stream making up the reaction medium can comprise, in addition to the HF and the chlorinated compound, additional compounds, in particular other halohydrocarbons or halohydroolefins.

The duration of the reaction stage is typically from 10 to 2000 hours, preferably from 50 to 500 hours and more particularly preferably from 70 to 300 hours.

According to the invention, the proportion of oxygen optionally present in the reaction medium is less than 0.05 mol % with respect to the chlorinated compound, more preferably less than 0.02 mol % or less than 0.01 mol %. Traces of oxygen may possibly be present but the fluorination stage is preferably carried out essentially in the absence of oxygen or in the complete absence of oxygen.

Preferably, the proportion of any oxidizing agent (such as oxygen and chlorine) optionally present in the reaction medium is less than 0.05 mol % with respect to the chlorinated compound, more preferably less than 0.02 mol % or less than 0.01 mol %. Traces of oxidizing agent may possibly be present, but the stage is preferably carried out essentially in the absence of oxidizing agent or in the complete absence of oxidizing agent.

The stream of products resulting from the stage of fluorination of the chlorinated compound to give HFO-1234 can be subjected to appropriate treatments (distillation, washing, etc.) in order to recover the HFO-1234 in the purified form and to separate it from the other compounds present (HCl, unreacted HF, unreacted chlorinated compound, other organic compounds). One or more streams can be subject to a recycling.

The HCl in particular can be subject to a purification according to the process described in the application FR 13/61736, to which reference is expressly made.

Regeneration of the Catalyst

In each reactor used for the implementation of the fluorination of the chlorinated compound to give HFO-1234, said fluorination can be alternated with phases of regeneration of the catalyst, in the presence of oxygen.

It is possible, for example, to pass from the reaction phase to the regeneration phase when the conversion of the chlorinated compound falls below a predetermined threshold, for example 50%.

If need be, beforehand, a transition period consisting in decompressing the reaction gas phase is provided. It can be followed by a phase of flushing with an inert gas or else by placing under vacuum with the aim of completely removing the reactants present.

The regeneration stream preferably contains at least 1 mol % of oxygen in total. It can be pure air but the stream can also contain an inert gas of use in providing a degree of dilution, for example nitrogen, argon, helium or else hydrofluoric acid in proportions varying from 0 to 95%, preferably from 5 to 85% and more particularly preferably from 10 to 80%. The flow rate of the regeneration stream is preferably kept sufficiently high to prevent external diffusional conditions.

The temperature in the regeneration stage has a value, for example, from 100 to 500° C., preferably from 200 to 450° C. and more particularly preferably from 250 to 400° C. It may be practical to carry out the regeneration at the same temperature as the reaction.

The pressure in the regeneration stage has a value, for example, from atmospheric pressure to 15 bar absolute. It is preferably approximately equal to atmospheric pressure.

The duration of the regeneration stage is typically from 10 to 2000 hours, preferably from 50 to 500 hours and more particularly preferably from 70 to 300 hours.

The regeneration can be carried out cocurrentwise or countercurrentwise with respect to the direction of the stream used during the reaction period.

This regeneration stage makes it possible to recover the initial activity of the catalyst. Several cycles can thus be linked together without significantly detrimentally affecting the activity of the catalyst, which makes it possible to increase its lifetime.

On conclusion of the regeneration stage, the reactor can be placed under vacuum so as to remove the inert gases and the oxygen introduced, prior to the reintroduction of the organic compounds.

Plants According to the Invention for the Implementation of the Fluorination Stage Described Above The fluorination stage described above can be carried out with a single reactor. In this case, the latter is operated alternately in reaction and in regeneration. Production is then noncontinuous.

Otherwise, the fluorination stage described above can be carried out with a plurality of reactors, for example two, three or more than three reactors. In this case, it is possible to operate at least one reactor in reaction while at least one other is operated in regeneration, and thus optionally to provide continuous production.

Figure 1B:
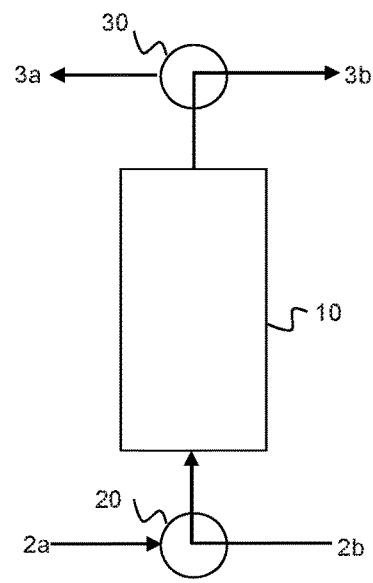

Referring to FIGS. 1a and 1b, an embodiment with just one reactor is described.

The plant then comprises a reactor 10, capable of being fed either by a system 2a for feeding with reaction stream or by a system 2b for feeding with regeneration stream.

Both a system 3a for collecting a stream of products and a system 3b for collecting a stream of gases resulting from the regeneration are connected at the outlet of the reactor 10.

"System for feeding" and "system for collecting" are understood to mean a single pipe or an assembly of several pipes.

A system 20 of valves at the inlet and a system 30 of valves at the outlet are provided in order to make it possible to switch between the respective systems for feeding and for collecting.

During the reaction stage (FIG. 1a), the system 20 of valves at the inlet is positioned in order for the reactor 10 to be fed by the system 2a for feeding with reaction stream, and the system 30 of valves at the outlet is positioned in order for the reactor 10 to feed the system 3a for collecting a stream of products, which directs the stream of products toward units for the downstream treatment of the production gases.

During the regeneration stage (FIG. 1b), the system 20 of valves at the inlet is positioned in order for the reactor 10 to be fed by the system 2b for feeding with regeneration stream, and the system 30 of valves at the outlet is positioned in order for the reactor 10 to feed the system 3b for collecting a stream of gases resulting from the regeneration, which directs the stream of gases resulting from the regeneration towards units for the downstream treatment of these gases.

The reactor 10 alternately links together periods of production and of regeneration sequentially. Production is noncontinuous.

Figure 2A:
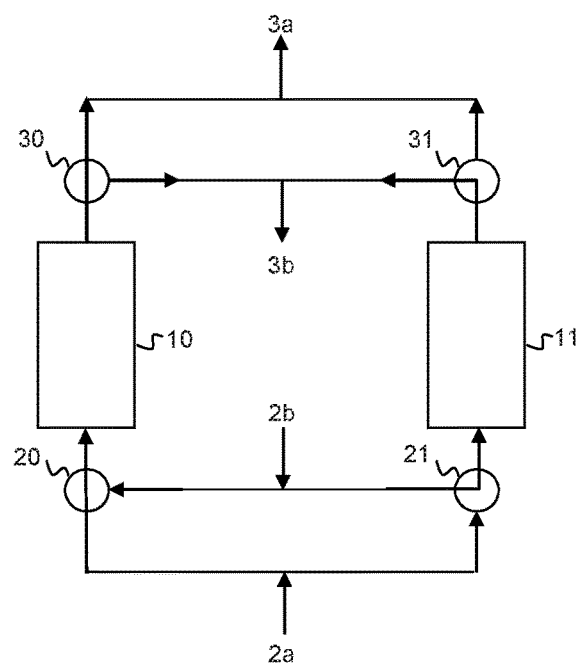
FIGS. 2a and 2b diagrammatically represent an embodiment of a plant according to the invention with two catalytic fluorination reactors, in two different operating configurations.
Figure 2B:
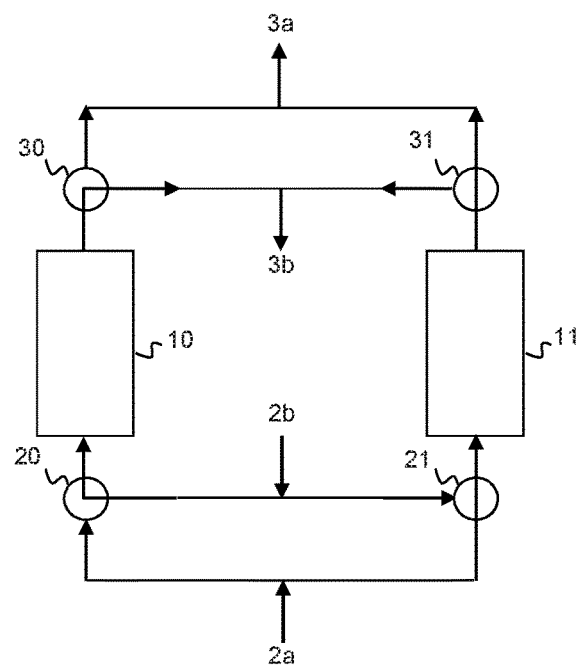

Referring to FIGS. 2a and 2b, an embodiment with two reactors is now described.

In a first configuration (FIG. 2a), the reaction stage is carried out in a first reactor 10 and the regeneration stage is carried out in a second reactor 11. In a second configuration (FIG. 2b), the reaction stage is carried out in the second reactor 11 and the regeneration stage is carried out in the first reactor 10. In this way, production is continuous.

Each reactor 10, 11 is provided with a system 20, 21 of valves at the respective inlet and also with a system 30, 31 of valves at the respective outlet in order to make it possible to pass from one configuration to the other. It is possible to provide for the system 2a for feeding with reaction stream, the system 2b for feeding with regeneration stream, the system 3a for collecting a stream of products and the system 3b for collecting a stream of gases resulting from the regeneration to be shared by the two reactors 10, 11, as illustrated, or else to provide separate systems dedicated to each reactor 10, 11.

Figure 3:
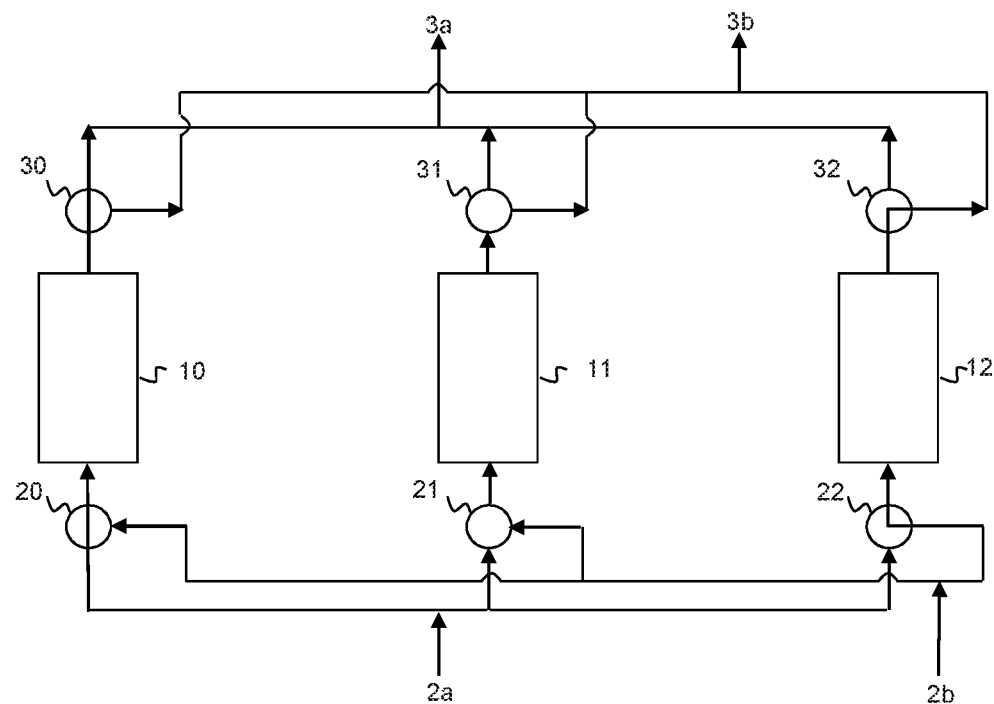
FIG. 3 diagrammatically represents an embodiment of a plant according to the invention with three catalytic fluorination reactors, in a particular operating configuration.

Referring to FIG. 3, an embodiment with three reactors is now described.

In the configuration illustrated, the reaction stage is carried out in a first reactor 10, a second reactor 11 is waiting and the regeneration stage is carried out in a third reactor 12. The waiting stage is a state in which the reactor has been regenerated and is ready to be used again in the reaction. In other non-illustrated configurations, the states of the reactors 10, 11, 12 are switched around. In this way, continuous production can be ensured.

Each reactor 10, 11, 12 is provided with a system 20, 21, 22 of valves at the respective inlet and also with a system 30, 31, 32 of valves at the respective outlet in order to make it possible to pass from one configuration to the other. It is possible to provide for the system 2a for feeding with reaction stream, the system 2b for feeding with regeneration stream, the system 3a for collecting a stream of products and the system 3b for collecting a stream of gases resulting from the regeneration to be shared by the three reactors 10, 11, 12 as illustrated or else to provide distinct systems dedicated to each reactor 10, 11, 12.

In the embodiments of FIGS. 1a, 1b, 2a, 2b and 3, the streams in the reactors are oriented in the same direction for the fluorination and for the regeneration.

According to alternative forms, the streams in the reactors can be oriented in reverse directions between the fluorination and the regeneration.

Figure 4A:
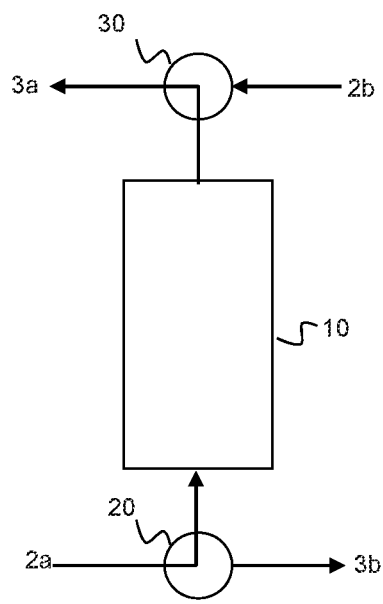
FIGS. 4a and 4b diagrammatically represent an embodiment of a plant according to the invention with just one catalytic fluorination reactor, in two different operating configurations.
Figure 4B:
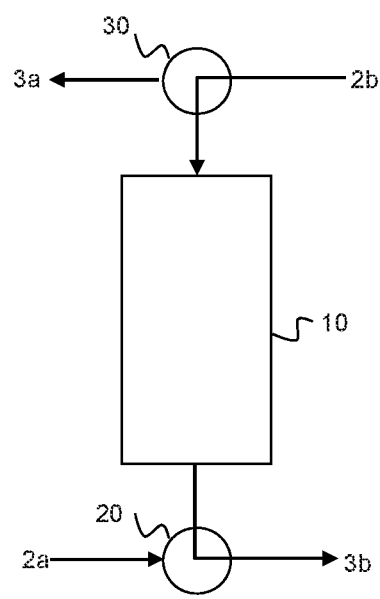

Thus, an embodiment is represented in FIGS. 4a and 4b with just one reactor 10 which is analogous to the embodiment of FIGS. 1a and 1b, except that the streams are reversed between the fluorination and the regeneration. For example, if the system 2a for feeding with reaction stream feeds the reactor 10 at the bottom, then the system 2b for feeding with regeneration stream feeds the reactor 10 at the top (or vice versa). Likewise, if the system 3a for collecting a stream of products is connected at the top of the reactor 10, then the system 3b for collecting a stream of gases resulting from the regeneration is connected at the bottom of the reactor 10 (or vice versa).

Figure 5A:
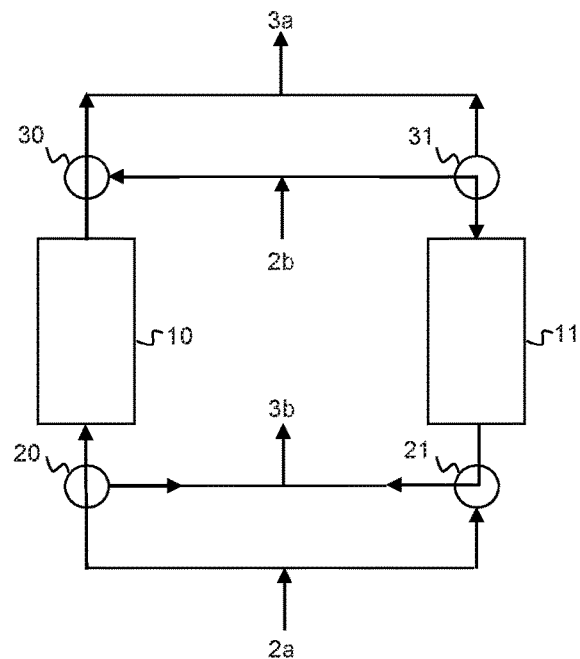
FIGS. 5a and 5b diagrammatically represent an embodiment of a plant according to the invention with two catalytic fluorination reactors, in two different operating configurations.
Figure 5B:
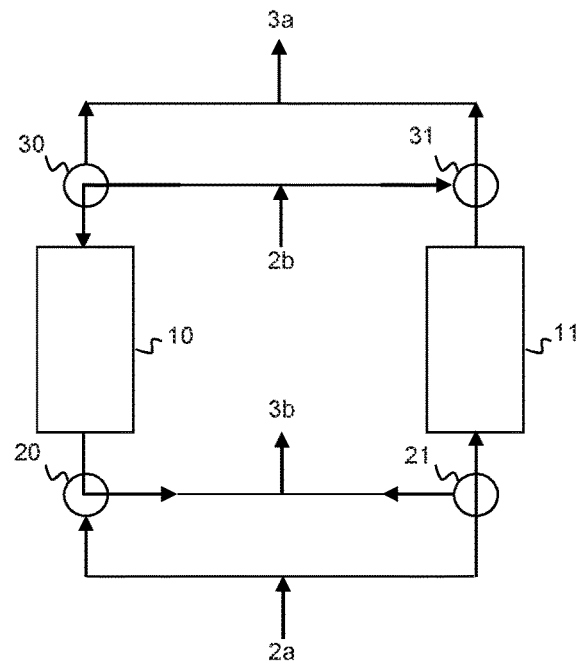

Likewise, an embodiment is represented in FIGS. 5a and 5b with two reactors 10, 11 which is analogous to the embodiment of FIGS. 2a and 2b, except that the streams are reversed between the fluorination and the regeneration. For example, if the system 2a for feeding with reaction stream feeds the reactors 10, 11 at the bottom, then the system 2b for feeding with regeneration stream feeds the reactors 10, 11 at the top (or vice versa). Likewise, if the system 3a for collecting a stream of products is connected at the top of the reactors 10, 11, then the system 3b for collecting a stream of gases resulting from the regeneration is connected at the bottom of the reactors 10, 11 (or vice versa).

Figure 6:
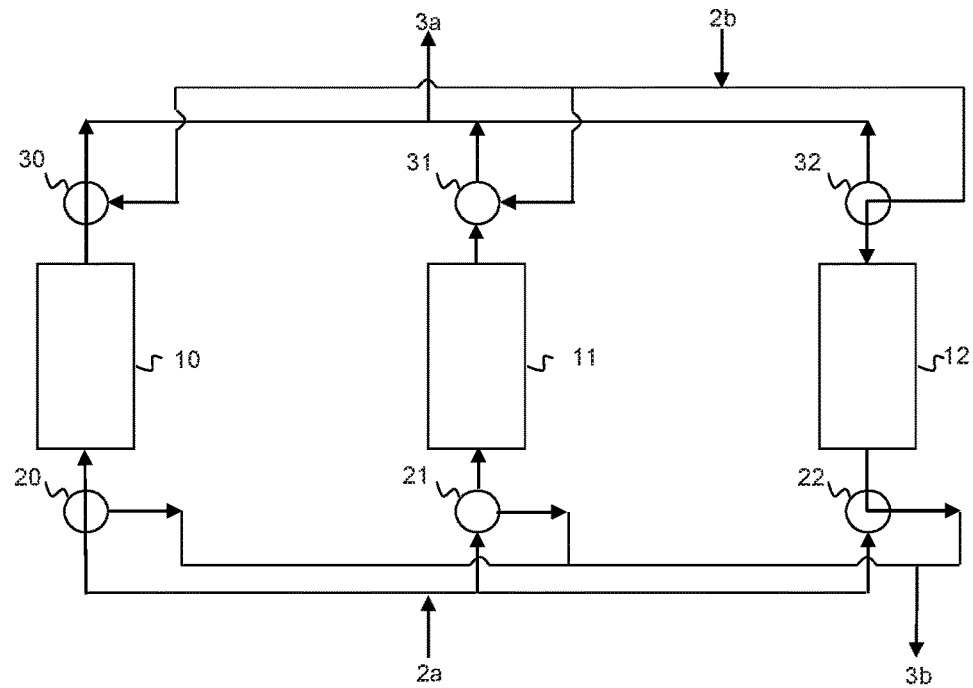
FIG. 6 diagrammatically represents an embodiment of a plant according to the invention with three catalytic fluorination reactors, in a particular operating configuration.

Likewise, an embodiment is represented in FIG. 6 with three reactors 10, 11, 12 which is analogous to the embodiment of FIG. 3, except that the streams are reversed between the fluorination and the regeneration. For example, if the system 2a for feeding with reaction stream feeds the reactors 10, 11, 12 at the bottom, then the system 2b for feeding with regeneration stream feeds the reactors 10, 11, 12 at the top (or vice versa). Likewise, if the system 3a for collecting a stream of products is connected at the top of the reactors 10, 11, 12, then the system 3b for collecting a stream of gases resulting from the regeneration is connected at the bottom of reactors 10, 11, 12 (or vice versa).

Processes According to the Invention in Several Stages

In some embodiments, the invention provides several successive reaction stages and preferably: first a preliminary stage of the manufacture of the chlorinated compound mentioned above; then, subsequently, the stage of fluorination of the chlorinated compound to give HFO-1234.

Preferably, the preliminary stage is itself a fluorination stage.

In this case, this stage converts a preliminary compound into the abovementioned chlorinated compound. In such a case, it should be noted that the chlorinated compound comprises at least one fluorine atom (since it results from a fluorination stage) and also at least one chlorine atom (since it is subsequently subjected to the fluorination stage described above in order to provide HFO-1234).

The "preliminary compound" is advantageously an organic compound (preferably having three carbon atoms) which comprises at least two chlorine atoms (and which comprises more chlorine atoms than the "chlorinated compound").

The preliminary compound can preferably be a propane or a propene having substituents chosen from F, Cl, I and Br (preferably from F and Cl) and comprising at least two Cl substituents. A propane is more particularly preferred.

It is understood that "preliminary compound" is also understood to mean mixtures of compounds.

According to a preferred embodiment, the preliminary compound is HCC-240db or HCC-240aa or a mixture of the two and the chlorinated compound is HCFO-1233xf, in order to produce HFO-1234yf.

According to yet another embodiment, the preliminary compound is HCFC-243db and the chlorinated compound is HCFO-1233xf, in order to produce HFO-1234yf.

According to yet another embodiment, the preliminary compound is HCO-1230xa or HCO-1230xf or a mixture of these two compounds and the chlorinated compound is HCFO-1233xf, in order to produce HFO-1234yf.

The conversion of the preliminary compound into the chlorinated compound can be a direct conversion or an indirect conversion (that is to say, involving an intermediate product).

It is possible to carry out the fluorination of the preliminary compound to give a chlorinated compound in the liquid phase. However, preferably, the fluorination is a gas-phase fluorination, in the presence of a fluorination catalyst. It can be carried out in one or more fluorination reactors in series or in parallel.

The fluorination catalyst can be of the same type as described above for the fluorination of the chlorinated compound to give HFO-1234. The above description relating to the activation of the catalyst also applies.

The reaction for the fluorination in the gas phase of the preliminary compound to give a chlorinated compound can in particular be carried out:

- with an HF/organic compounds molar ratio of 3:1 to 100:1, preferably of 5:1 to 50:1 (the term "organic compounds" denotes all of the compounds of the reaction medium comprising one or more carbon atoms);
- at an absolute pressure ranging from 0.1 to 50 bar, preferably from 0.3 to 15 bar;
- with a contact time of 1 to 100 s, preferably of 1 to 50 s and more particularly of 2 to 40 s (catalyst volume divided by the total incoming stream, adjusted to the operating temperature and pressure);
- at temperature (temperature of the catalyst bed) of 100 to 500° C., preferably of 200 to 450° C. and more particularly of 250 to 400° C.

The stream making up the reaction medium can comprise, in addition to the HF and the preliminary compound, additional compounds, in particular other halohydrocarbons or halohydroolefins. The stream can, for example, already comprise an HFO-1234 fraction.

According to a preferred embodiment, there is no or essentially no oxygen (and optionally there is no or essentially no other oxidizing agent) in the reaction medium.

Thus, the presence of oxygen or of oxidizing agent in the subsequent fluorination stage is also avoided, without having to carry out an intermediate separation of a stream of oxygen or oxidizing agent.

The duration of the stage of reaction of the preliminary compound to give a chlorinated compound is typically from 10 to 2000 hours, preferably from 50 to 500 hours and more particularly preferably from 70 to 300 hours.

On conclusion of this reaction stage, a stream of products is collected which comprises in particular chlorinated compound, unreacted preliminary compound, HF, HCl, optionally HFO-1234 and optionally secondary products, such as in particular 1,1,1,2,2-pentafluoropropane (HFC-245cb).

This stream of products can subsequently directly feed the stage of fluorination of the chlorinated compound to give HFO-1234yf described above.

Alternately, this stream of products can be separated, for example by distillation, to provide, for example, a first stream comprising HCl and optionally HFO-1234 and a second stream comprising HF and chlorinated compound. The distillation can, for example, be carried out at a temperature of −90 to 150° C., preferably of −85 to 100° C., and at a pressure of 0.1 to 50 bar abs and preferably of 0.3 to 5 bar abs.

The first stream can be directed to a unit for the production of acid in order to produce HCl and HFO-1234. The HFO-1234 and the intermediate products can be recovered by known means, such as extraction, washing, separation by settling and preferably distillation means.

It should be noted that, according to the invention, at least one of the two fluorination stages described above is alternated with a stage of regeneration of the reactor or reactors with a stream of oxidizing agent, as described above in connection with the fluorination of the chlorinated compound to give HFO-1234. The above description thus applies by analogy (including that relating to the different possible plants illustrated in FIGS. 1a to 6):

- either to the regeneration alternated with the fluorination of the preliminary compound to give a chlorinated compound;
- or to the regeneration alternated with the fluorination of the chlorinated compound to give HFO-1234;
- or both to the regeneration alternated with the fluorination of the preliminary compound to give a chlorinated compound and to the regeneration alternated with the fluorination of the chlorinated compound to give HFO-1234.

Depending on the reaction conditions and the nature of the catalyst, the tendency of the catalyst to become deactivated can be different, hence these various possible scenarios.

Processes for the Manufacture of HFO-1234yf in Two Stages

A description is now given of various embodiments in connection with the manufacture of HFO-1234yf in two stages starting from HCC-240db (it being understood that it is also possible instead to use HCC-240aa or a mixture of the two): a first stage of conversion of HCC-240db to give HCFO-1233xf and then a second stage of conversion of HCFO-1233xf to give HFO-1234yf, which stages are carried out in successive reactors.

Figure 7:
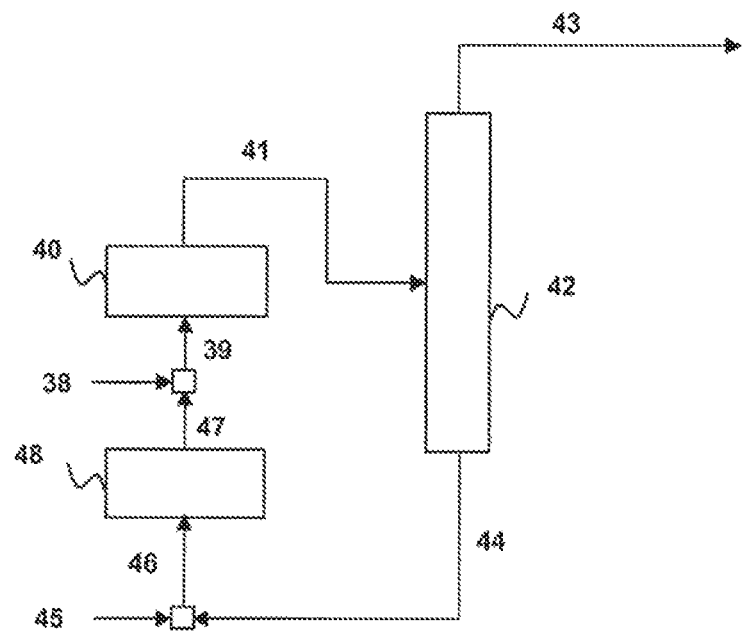
FIGS. 7 to 11 diagrammatically represent embodiments of plants according to the invention for the production of HFO-1234yf in two stages.

Referring to FIG. 7, according to one embodiment, a plant according to the invention can thus comprise a first fluorination reactor 40 for the implementation of the stage of preparation of HCFO-1233xf. It is understood that it is also possible instead to use a plurality of reactors, operating in series and/or in parallel.

This first fluorination reactor 40 is fed by a first system 39 for feeding with reaction medium (comprising HF and HCC-240db).

A system 41 for collecting a stream of products is positioned at the outlet of the first fluorination reactor 40, which collecting system feeds a separation unit 42. This separation unit 42 can in particular be a distillation unit as described above.

A first collecting pipe 43 and a second collecting pipe 44 are provided at the outlet of the separation unit 42. The first collecting pipe 43 is configured in order to transport a stream comprising in particular HCl and HFO-1234yf and the second collecting pipe 44 is configured in order to transport a stream comprising in particular HF and HCFO-1233xf.

The first collecting pipe 43 feeds additional treatment units, not represented, which can in particular comprise a unit for the production of acid, while the second collecting pipe 44 provides for recycling toward at least one second gas-phase fluorination reactor 48 which is used for the fluorination of HCFO-1233xf to give HFO-1234yf. This second collecting pipe 44 can thus also be described as a recycling pipe. This second reactor 48 is fed by a second system 46 for feeding with reaction medium, which itself is fed by the second collecting pipe 44, on the one hand, and by a system 45 for feeding with HF, on the other hand.

An intermediate collecting system 47 is connected at the outlet of the second reactor 48. This collecting system in turn feeds the first system 39 for feeding with reaction medium of the first reactor 40. HCC-240db is supplied by a system 38 for feeding with HCC-240db.

Preferably, in this plant and in all the fluorination stages, the proportion of oxygen optionally present in the streams is less than 0.05 mol % with respect to the predominant organic compound, more preferably less than 0.02 mol % or less than 0.01 mol %. Traces of oxygen may possibly be present but, preferably, the whole of the process for the fluorination of HCC-240db to give HFO-1234yf is carried out essentially in the absence of oxygen or in the complete absence of oxygen.

Preferably, the proportion of any oxidizing agent (such as oxygen and chlorine) optionally present in the reaction medium is less than 0.05 mol % with respect to the predominant organic compound, more preferably less than 0.02 mol % or less than 0.01 mol %. Traces of oxidizing agent may optionally be present but, preferably, the entire process for the fluorination of HCC-240db to give HFO-1234yf is carried out essentially in the absence of oxidizing agent or in the complete absence of oxidizing agent.

In accordance with the invention, regeneration of the catalyst is provided, alternating with the fluorination. This regeneration can concern either the first reactor 40 or the second reactor 48 or both the reactors 40, 48. The regeneration is carried out as described above, using a stream of oxidizing agent. The means necessary for the regeneration are not represented in FIG. 7 but are analogous to those described above.

Figure 8:
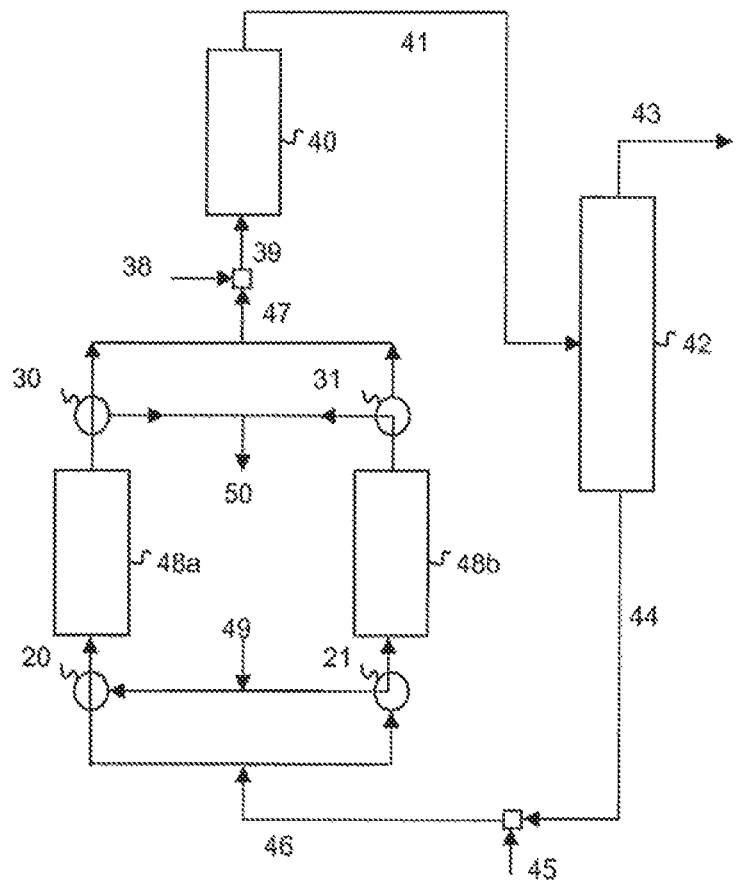

An alternative form is illustrated in FIG. 8. It is identical to the embodiment of FIG. 7 except that, instead of a single second reactor 48, two second reactors 48a, 48b are provided. These are configured to operate alternately in fluorination mode and in regeneration mode, as described above in connection with FIGS. 2a and 2a.

Thus, by controlling a system 20, 21 of valves at the inlet and a system 30, 31 of valves at the outlet, it is arranged that:

- in one phase, one of the second reactors 48a operates in fluorination mode, that is to say is fed by the second system 46 for feeding with reaction medium and feeds the intermediate collecting system 47, while the other of the second reactors 48b operates in regeneration mode, that is to say is fed by a system 49 for feeding with regeneration stream and itself feeds a system 50 for collecting a stream of gases resulting from the regeneration;
- in another phase, the configurations of the two reactors 48a, 48b are reversed.

It should be noted that, in FIG. 8, a regeneration which is carried out in the same direction as the fluorination has been represented. However, the streams can also be reversed, as described in connection with FIGS. 5a and 5b.

Figure 9:
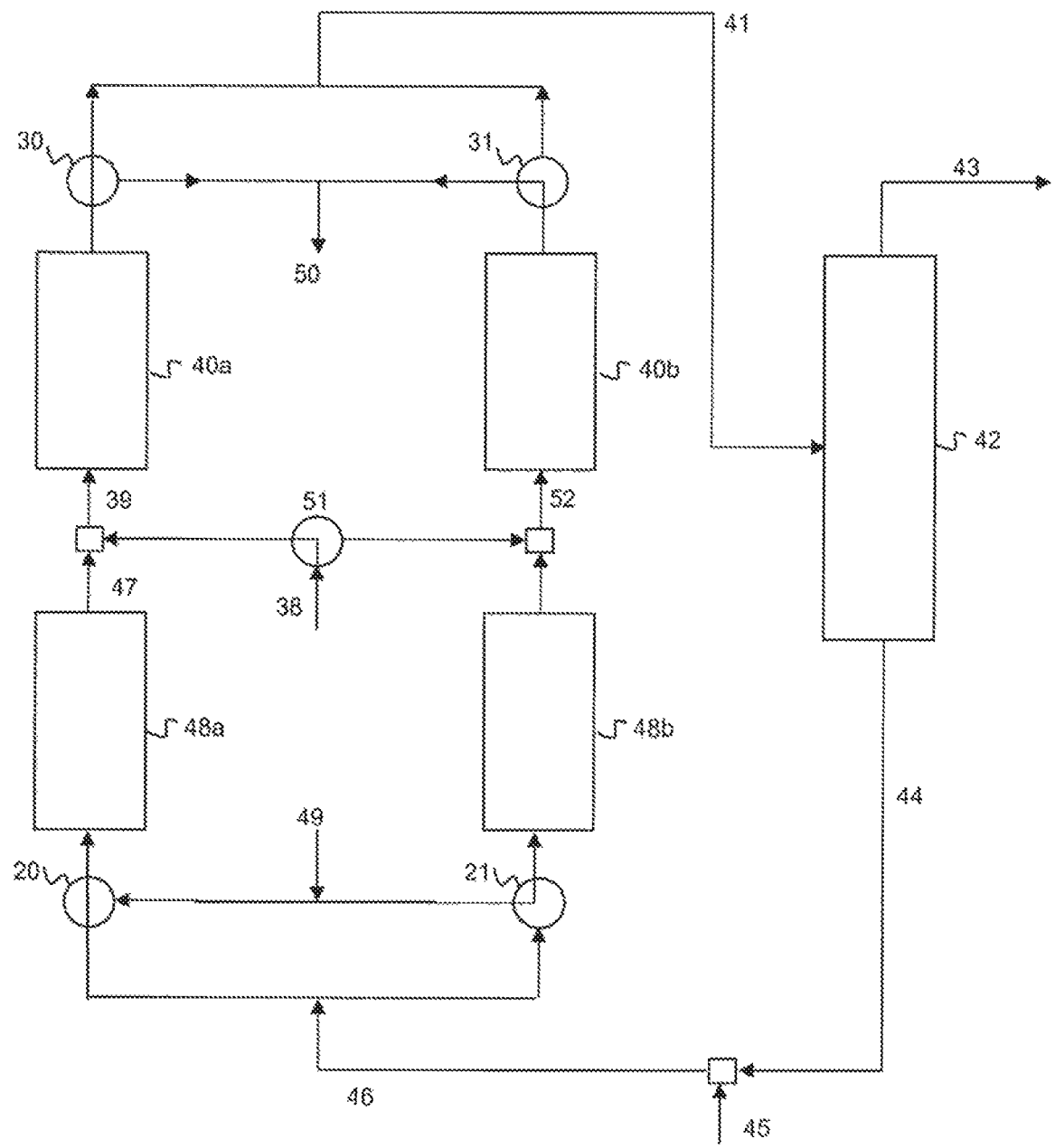

Another alternative form is illustrated in FIG. 9. It is identical to the embodiment of FIG. 8 except that not only are two second reactors 48a, 48b provided but also two first reactors 40a, 40b are provided instead of a single first reactor. These two first reactors are configured in order to operate alternately in fluorination mode and in regeneration mode, as described above in connection with FIGS. 2a and 2b.

In a first phase, which is that illustrated in the figure, the second system 46 for feeding with reaction medium feeds one of the two second reactors 48a. The intermediate collecting system 47 is connected at the outlet of this second reactor 48a, which makes it possible to collect a stream of intermediate products. This feeds the first system 39 for feeding with reaction medium (also with the system 38 for feeding with HCC-240db), which itself feeds one of the two first reactors 40a.

The system 41 for collecting a stream of products is connected at the outlet of this first reactor 40a.

The system 49 for feeding with regeneration stream feeds the other second reactor 48b, preferably simultaneously. A system 52 for the intermediate collecting of a stream of gases resulting from the regeneration is connected at the outlet of this second reactor 48b and feeds, at the inlet, the other first reactor 40b. The system 50 for the intermediate collecting of a stream of gases resulting from the regeneration is connected at the outlet of this first reactor 40b.

Alternatively, intermediate feeding with an additional regeneration stream can be provided between the two reactors 48b, 40b. Alternatively again, regeneration by streams independent of these two reactors 48b, 40b can be provided.

Alternately again, regeneration with streams in the reverse direction to those of the fluorination can be provided, according to the principles of FIGS. 5a and 5b.

In a second phase, not illustrated, the fluorination and regeneration configurations are reversed between the reactors.

The change from one configuration to the other is provided by means of an assembly of valves: in the example illustrated, the valves are valves 20, 21 at the inlet 20, 21, which are located upstream of the second reactors 48a, 48b, valves at the outlet, which are located downstream of the first reactors 40a, 40b, and finally an HCC-240db valve 51 located at the system 38 for feeding with HCC-240db.

Figure 10:
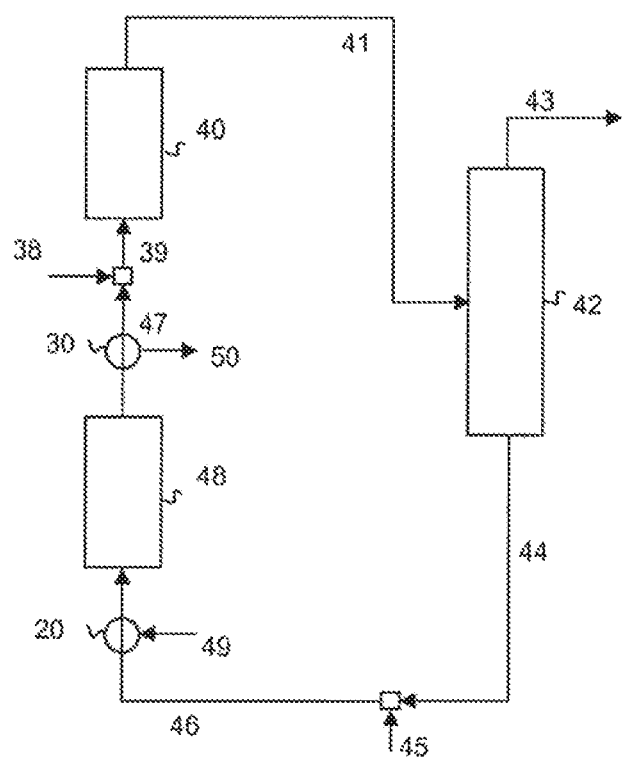

Another alternative form is illustrated in FIG. 10. It is analogous to the embodiment of FIG. 7. In this alternative form, sequential regeneration with respect to the fluorination (and not simultaneous regeneration) is provided, on just one of the two reactors, namely the second reactor 48.

To this end, the system 49 for feeding with regeneration stream is connected at the inlet of the second reactor 48 and the system 50 for collecting a stream of gases resulting from the regeneration is connected at the outlet of the second reactor 48. A system 20 of valves at the inlet and a system 30 of valves at the outlet makes it possible to switch the second reactor 48, either into fluorination mode or into regeneration mode.

It should be noted that the fluorination and regeneration streams can be in the same direction or in the opposite direction.

It should also be noted that it is also possible to provide the same means for ensuring the regeneration at the first reactor 40, either in addition to or as a replacement for the regeneration means of the second reactor 48.

Figure 11:
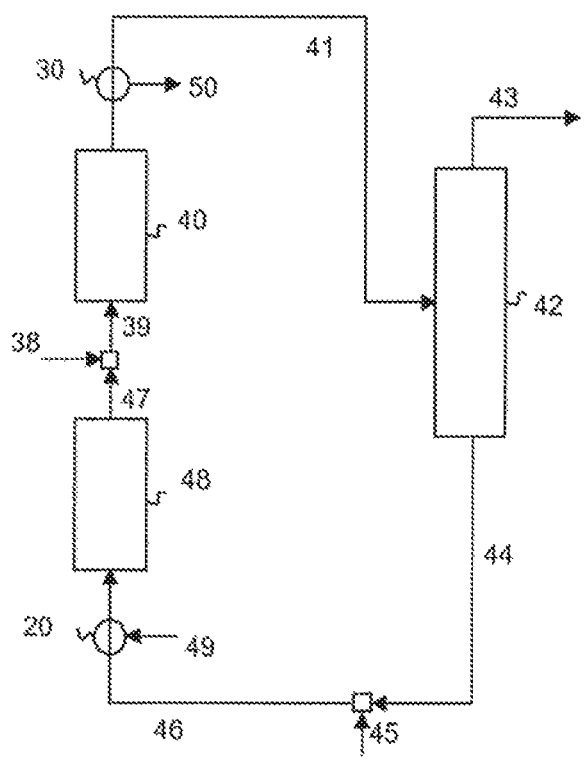

Another alternative form is illustrated in FIG. 11. It is analogous to the embodiment of FIG. 7. In this alternative form, sequential regeneration with respect to the fluorination (and not simultaneous regeneration) is provided, on the two reactors simultaneously, namely the first reactor 40 and the second reactor 48.

To this end, the system 49 for feeding with regeneration stream is connected at the inlet of the second reactor 48 and the system 50 for collecting a stream of gases resulting from the regeneration is connected at the outlet of the first reactor 40. A system 20 of valves at the inlet and a system 30 of valves at the outlet makes it possible to switch the reactors 40, 48, either into fluorination mode or into regeneration mode.

It should be noted that the fluorination and regeneration streams can be in the same direction or in the opposite direction.

Everything which has been described here in connection with the preparation of HFO-1234yf in two stages can be read analogously by replacing HCC-240db with another starting preliminary compound (and by replacing HCFO-1233xf with another chlorinated compound). Likewise, that which has been described here can be applied analogously to the preparation of other HFO-1234 compounds.

Another possibility for the implementation of the invention consists in: on the one hand, producing chlorinated compound from the preliminary compound (for example HCFO-1233xf from HCC-240db or similar) and, on the other hand, producing HFO-1234 from chlorinated compound (for example HFO-1234yf from HCFO-1233xf), this being done independently and separately, for example by isolating, storing and/or transporting the chlorinated compound between the two stages, and by carrying out the alternating regeneration according to the invention on the first stage or the second stage or both, independently.

Products Obtained

The consequence of the absence or virtual absence of oxygen during the reaction phase is the decrease in the content of impurities related to the combustion or decomposition reactions of the molecules. The impurities are carbon oxides or dioxides and also the molecules containing fewer carbon atoms than the starting chlorinated product.

Thus, the invention makes it possible to obtain a stream of HFO-1234 (and in particular of HFO-1234yf) containing less chloromethane (HCC-40) and 1,1-difluoroethane (HFC-152a) than in the state of the art. In point of fact, these compounds form an azeotrope with HFO-1234yf, which makes them difficult to purify.

The invention also makes it possible to obtain a stream of HFO-1234 (and in particular of HFO-1234yf) containing less fluoromethane (HFC-41) and difluoromethane (HFC-32) than in the state of the art. In point of fact, it is known that these compounds are extremely flammable.

The molar proportion of each of these compounds in the HFO-1234 stream is thus preferably less than 100 ppm and more particularly less than 50 ppm.

According to one embodiment, this stream contains HFO-1234 (preferably HFO-1234yf) and also from 1 to 50 ppm of HCC-40, from 1 to 50 ppm of HFC-152a, from 1 to 50 ppm of HFC-41 and from 1 to 50 ppm of HFC-32.

According to one embodiment, this stream is essentially devoid and preferably is devoid of HCC-40.

According to one embodiment, this stream is essentially devoid and preferably is devoid of HFC-152a.

According to one embodiment, this stream is essentially devoid and preferably is devoid of HFC-41.

According to one embodiment, this stream is essentially devoid and preferably is devoid of HFC-32.

According to one embodiment, this stream contains at least 98% of HFO-1234, preferably at least 99% and in particular at least 99.5%, indeed even at least 99.8%, by weight.

The HFO-1234 stream under consideration is either the stream obtained at the outlet of the reactor for the fluorination of the chlorinated compound to give HFO-1234 (stream withdrawn in the system 3a for collecting a stream of product in the figures), or the stream obtained at the outlet of the separation unit (stream withdrawn in the first collecting pipe 43 in the figures), or the stream obtained later still after separation of the HFO-1234 and the hydrochloric acid.

Furthermore, the absence or virtual absence of oxygen also makes it possible to obtain a stream of hydrochloric acid with a greater purity which makes possible easier recovery in value. Thus, the stream of hydrochloric acid recovered after separation from HFO-1234 is preferably devoid (or essentially devoid) of trifluoroacetic acid, of $COF_2$ or of COFCl.

EXAMPLES

The following examples illustrate the invention without limiting it.

A gas-phase fluorination reactor equipped with feeding with HF, with feeding with fresh organic products, with available feeding for the cofeeding of another gaseous compound and with a pipe for feeding resulting from the recycling of the unconverted reactants is available.

The outflow of the gas stream resulting from this reactor is sent to a pipe cooled with a jacket which makes it possible to cool and partially condense the reaction products before they are introduced into the distillation column. The partially condensed stream is thus conveyed to a distillation column with a height of 1.5 m filled with a metal packing of Sulzer type which facilitates the exchanges between the ascending gas stream and the descending liquid reflux. The distillation column is equipped with a boiler at the column bottom and with a condensation system at the top. This separation unit makes it possible to separate a top stream which predominantly consists of the desired product (HFO-1234yf) and of the byproduct HCl. Greater or lesser amounts of byproduct HFC-245cb are also present. The column bottom stream predominantly consists of HF and of unconverted reactant (HCFO-1233xf) and also of the byproduct HFC-245cb resulting from the addition of HF to HFO-1234yf. This column bottom stream is subsequently recycled to the gas-phase reactor. Traces of impurities are present in each of the streams.

180 ml of bulk chromium-based catalyst are introduced into the reactor made of Inconel. It is first subjected to a period of drying under 50 l/h of nitrogen at atmospheric pressure at 275° C. overnight. Subsequently, while maintaining the nitrogen and still at 275° C., a stream of HF is gradually added until a flow rate of 1 mol/h is obtained. This treatment is maintained overnight. The nitrogen is subsequently halted and the temperature of the oven is increased to 350° C. The treatment under pure HF is thus also maintained overnight. Finally, a treatment under 5 l/h of air is applied for at least 24 h.

Following the treatment for activation of the catalyst, the reactants HCFO-1233xf and HF are introduced into the recycling loop so as to fill this part of the plant while retaining a molar ratio of the hydrofluoric acid to the organic compound of 25. Initiation is carried out by feeding the liquid present in the recycling loop to the gas-phase reactor (a preheater ensures the prior vaporization of the reactants). The system subsequently gradually becomes equilibrated between the unconverted reactants, which are recycled, the products formed, which are discharged from and collected outside the system, and the fresh reactants, which are continuously fed so as to compensate exactly for the amount of products discharged. The level of liquid in the distillation column thus remains constant.

The conversion of the catalyst changes over time and gradually decreases. When the conversion falls below 50%, a regeneration treatment with air is applied to the catalyst. This treatment makes it possible to fully recover the initially activity of the catalyst.

The conversion is calculated from the molar content of HCFO-1233xf measured at the inlet of the reactor (sum of the recycling and fresh organic compound streams) and from the content of HCFO-1233xf measured at the outlet of the reactor.

Example 1—Catalytic Results in the Presence of Air

A test is carried out under the following operating conditions: the catalyst is freshly regenerated, the molar ratio of HF to the organic compounds is 25, the gas-phase contact time is 15 seconds, the temperature is 350° C. and 10 mol % of oxygen are added with respect to the sum of the organic compounds introduced. The conversion of the HCFO-1233xf obtained over time is given in table 1 below. During this test, the gas stream exiting from the top of the distillation column is analyzed by gas chromatography. The analysis is given in table 2 below (value as % of GC area).

Example 2—Catalytic Results Without Air

The procedure of example 1 is taken up again but without addition of supplementary oxygen to the gas phase. The results obtained for the conversion over time are given in table 1 below. The analysis of the gas stream exiting from the distillation column is given in table 2 below (value as % of GC area). The carbon oxides and the $C_1$ and $C_2$ impurities are markedly reduced. The purity of the sum of the desired product HFO-1234yf and of the recyclable byproduct HFC-245cb increases.

TABLE 1

| Example 1 | | Example 2 | |
| --- | --- | --- | --- |
| Time (h) | Conversion of HCFO-1233xf (%) | Time (h) | Conversion of HCFO-1233xf (%) |
| 4 | 78.6 | 15 | 77.6 |
| 8 | 77.4 | 19 | 78.5 |
| 12 | 76.3 | 24 | 77.8 |
| 16 | 77.2 | 27 | 78.3 |
| 21 | 78.7 | 31 | 76.9 |
| 28 | 76.2 | 35 | 74.5 |
| 32 | 76.8 | 39 | 72.8 |
| 36 | 76.9 | 43 | 71.7 |
| 40 | 75.9 | 48 | 72.7 |
| 48 | 75.6 | 51 | 72.9 |
| 52 | 73.4 | 55 | 73.2 |
| 60 | 73.4 | 59 | 73.6 |
| 64 | 72.1 | 63 | 74.1 |
| 71 | 70.2 | 71 | 70.9 |
| 80 | 67.8 | 82 | 70.9 |
| 84 | 65.0 | 86 | 69.4 |

TABLE 2

| Product detected | Example 1 | Example 2 |
| --- | --- | --- |
| CO | 3.2 | 0.22 |
| $CO_2$ | 1.39 | 0.04 |
| F23 | 0.13 | Nd |
| F41 | 0.06 | Nd |
| F32 | 0.03 | Nd |
| F125 | 0.17 | Nd |

TABLE 2-continued

| Product detected | Example 1 | Example 2 |
|---|---|---|
| Trifluoropropyne | 0.08 | 0.02 |
| F143a | 0.36 | 0.04 |
| F1234yf + 245cb | 93.19 | 98.03 |
| F40 | 0.26 | Nd |
| F152a | 0.02 | Nd |
| F1234zeE | 1.10 | 1.62 |
| F1233xf | 0.01 | Nd |

Nd: not detected

EMBODIMENTS

1. A process for the manufacture of tetrafluoropropene, comprising, alternately:
    at least one stage of reaction of a chlorinated compound with hydrofluoric acid in the gas phase, in the presence of a fluorination catalyst, the proportion of oxygen optionally present being less than 0.05 mol % with respect to the chlorinated compound;
    a stage of regeneration of the fluorination catalyst by bringing the fluorination catalyst into contact with a regeneration stream comprising an oxidizing agent.
2. The process as in embodiment 1, in which the stage of reaction of the chlorinated compound with hydrofluoric acid is carried out essentially in the absence of oxygen and preferably essentially in the absence of any oxidizing agent.
3. The process as in embodiment 1 or 2, in which the regeneration stream contains at least 1 mol % of oxygen with respect to the total regeneration stream.
4. The process as in one of embodiments 1 to 3, in which the stage of reaction of the chlorinated compound with hydrofluoric acid is carried out in a single reactor, separately in time with respect to the stage of regeneration of the fluorination catalyst.
5. The process as in one of embodiments 1 to 3, in which the stage of reaction of the chlorinated compound with hydrofluoric acid is carried out in at least one first reactor, simultaneously with the implementation of the stage of regeneration of the fluorination catalyst in at least one second reactor.
6. The process as in one of embodiments 1 to 5, in which the tetrafluoropropene is 2,3,3,3-tetrafluoropropene.
7. The process as in one of embodiments 1 to 5, in which the tetrafluoropropene is 1,3,3,3-tetrafluoropropene.
8. The process as in one of embodiments 1 to 7, in which the chlorinated compound is chosen from tetrachloropropenes, chlorotrifluoropropenes, pentachloropropanes and mixtures of these.
9. The process as in one of embodiments 1 to 6 and 8, in which the chlorinated compound is 2-chloro-3,3,3-trifluoropropene and the tetrafluoropropene is 2,3,3,3-tetrafluoropropene.
10. The process as in one of embodiments 1 to 6 and 8, in which the chlorinated compound is 1,1,1,2,3-pentachloropropane and/or 1,1,2,2,3-pentachloropropane and the tetrafluoropropene is 2,3,3,3-tetrafluoropropene.
11. The process as in one of embodiments 1 to 5 and 7 and 8, in which the chlorinated compound is 1-chloro-3,3,3-trifluoropropene and the tetrafluoropropene is 1,3,3,3-tetrafluoropropene.
12. The process as in one of embodiments 1 to 11, comprising:
    a preliminary stage of manufacture of the chlorinated compound, which is preferably a preliminary stage of reaction of a preliminary compound with hydrofluoric acid in the gas phase, in the presence of a preliminary fluorination catalyst, the proportion of oxygen optionally present being less than 0.05 mol % with respect to the preliminary compound.
13. The process as in embodiment 12, in which the preliminary stage of reaction is carried out alternately with:
    a stage of regeneration of the preliminary fluorination catalyst by bringing the preliminary fluorination catalyst into contact with a regeneration stream comprising an oxidizing agent.
14. The process as in either of embodiments 12 and 13, in which the preliminary compound is 1,1,1,2,3-pentachloropropane and/or 1,1,2,2,3-pentachloropropane, the chlorinated compound is 1-chloro-3,3,3-trifluoropropene and the tetrafluoropropene is 2,3,3,3-tetrafluoropropene.
15. The process as in one of embodiments 12 to 14, comprising:
    the collecting of a stream of products on conclusion of the preliminary reaction stage;
    the separation of the stream of products into a first stream comprising hydrochloric acid and tetrafluoropropene and a second stream comprising hydrofluoric acid and the chlorinated compound;
    the use of said second stream to carry out the stage of reaction of the chlorinated compound with hydrofluoric acid; and
    optionally, the collecting of a stream of products on conclusion of the stage of reaction of the chlorinated compound with hydrofluoric acid and the recycling of the latter in the preliminary reaction stage.
16. A plant for the manufacture of tetrafluoropropene, comprising at least one gas-phase fluorination reactor (10) comprising a bed of fluorination catalyst, said gas-phase fluorination reactor (10) being configured in order to be fed alternately by:
    a system (2a) for feeding with reaction stream (2a) comprising a chlorinated compound and hydrofluoric acid, the proportion of oxygen optionally present in this reaction stream being less than 0.05 mol % with respect to the chlorinated compound; and
    a system (2b) for feeding with regeneration stream comprising an oxidizing agent.
17. The plant as in embodiment 16, in which the reaction stream is essentially devoid of oxygen and preferably of any oxidizing agent.
18. The plant as in embodiment 16 or 17, in which the regeneration stream contains at least 1 mol % of oxygen with respect to the total regeneration stream.
19. The plant as in one of embodiments 16 to 18, comprising a single reactor (10) configured in order to be fed alternately by the system (2a) for feeding with reaction stream and the system (2b) for feeding with regeneration stream.
20. The plant as in one of embodiments 16 to 18, comprising a plurality of reactors (10, 11, 12), each being configured in order to be fed alternately by a system (2a) for feeding with reaction stream and a system (2b) for feeding with regeneration stream.
21. The plant as in embodiment 20, configured so that, when a reactor (10) is fed by the system (2a) for feeding with reaction stream, another reactor (11) is fed by the system (2b) for feeding with regeneration stream.

22. The plant as in one of embodiments 16 to 21, configured so that:
the system (2a) for feeding with reaction stream feeds the reactor (10) at the bottom and the system (2b) for feeding with regeneration stream feeds the reactor (10) at the bottom; or
the system (2a) for feeding with reaction stream feeds the reactor (10) at the bottom and the system (2b) for feeding with regeneration stream feeds the reactor (10) at the top; or
the system (2a) for feeding with reaction stream feeds the reactor (10) at the top and the system (2b) for feeding with regeneration stream feeds the reactor (10) at the bottom; or
the system (2a) for feeding with reaction stream feeds the reactor (10) at the top and the system (2b) for feeding with regeneration stream feeds the reactor (10) at the top.

23. The plant as in one of embodiments 16 to 22, in which:
the tetrafluoropropene is 2,3,3,3-tetrafluoropropene; or
the tetrafluoropropene is 1,3,3,3-tetrafluoropropene.

24. The plant as in one of embodiments 16 to 23, in which the chlorinated compound is chosen from tetrachloropropenes, chlorotrifluoropropenes, pentachloropropanes and mixtures of these; and preferably:
the chlorinated compound is 2-chloro-3,3,3-trifluoropropene and the tetrafluoropropene is 2,3,3,3-tetrafluoropropene; or
the chlorinated compound is 1,1,1,2,3-pentachloropropane and/or 1,1,2,2,3-pentachloropropane and the tetrafluoropropene is 2,3,3,3-tetrafluoropropene; or
the chlorinated compound is 1-chloro-3,3,3-trifluoropropene and the tetrafluoropropene is 1,3,3,3-tetrafluoropropene.

25. The plant as in one of embodiments 16 to 24, comprising:
at least one unit for the manufacture of chlorinated compound, which preferably is at least one preliminary fluorination reactor (40); configured in order to be fed by:
a system (39) for feeding with reaction medium comprising a preliminary compound and hydrofluoric acid, the proportion of oxygen optionally present in this reaction stream being less than 0.05 mol % with respect to the preliminary compound.

26. The plant as in embodiment 25, in which the preliminary fluorination reactor (40) is also configured in order to be fed by a system (49) for feeding with regeneration stream comprising an oxidizing agent.

27. The plant as in either of embodiments 25 and 26, in which the preliminary compound is 1,1,1,2,3-pentachloropropane and/or 1,1,2,2,3-pentachloropropane, the chlorinated compound is 1-chloro-3,3,3-trifluoropropene and the tetrafluoropropene is 2,3,3,3-tetrafluoropropene.

28. The plant as in one of embodiments 16 to 27, comprising:
at least one first catalytic fluorination reactor (40);
at least one second catalytic fluorination reactor (48);
a system (41) for collecting a stream of products connected at the outlet of the first catalytic fluorination reactor (40);
a separation unit (42) fed by the system (41) for collecting a stream of products;
a first collecting pipe (43) and a second collecting pipe (44) which are connected at the outlet of the separation unit (42), the first collecting pipe (43) being configured in order to transport a stream comprising hydrochloric acid and tetrafluoropropene and the second collecting pipe (44) being configured in order to transport a stream comprising hydrofluoric acid and chlorinated compound;
an intermediate collecting system (47) connected at the outlet of the second reactor (48);
a first system (39) for feeding with reaction medium configured in order to feed the first reactor (40), this being itself fed by the intermediate collecting system (47);
a second system (46) for feeding with reaction medium configured in order to feed the second reactor (48), this being itself fed by the second collecting pipe (44);
a system (49) for feeding with regeneration stream configured in order to feed the first reactor (40) and/or the second reactor (48); and
a system (50) for collecting a stream of gases stream resulting from the regeneration (50).

29. The plant as in embodiment 28, which comprises at least two second reactors (48a, 48b) configured so that, when one of these reactors (48a) is fed by the second system (46) for feeding with reaction stream, the other reactor (48b) is fed by the system (49) for feeding with regeneration stream.

30. The plant as in embodiment 28, which comprises at least two first reactors (40a, 40b) and two second reactors (48a, 48b) configured so that, when one of the first reactors (40a) and one of the second reactors (48a) are respectively fed by the first system (39) for feeding with reaction stream and the second system (46) for feeding with reaction stream, the other first reactor (40b) and the other second reactor (48b) are fed by the system (49) for feeding with regeneration stream; and which, preferably, is configured so that one and the same regeneration stream resulting from the system (49) for feeding with regeneration stream passes successively into the first reactor (40b) and then the second reactor (48b) or passes successively into the second reactor (48b) and then the first reactor (40b).

31. The plant as in embodiment 28, which comprises a single second reactor (48) configured in order to be fed sequentially either by the second system (46) for feeding with reaction stream or by the system (49) for feeding with regeneration stream.

32. The plant as in embodiment 28, which comprises a single first reactor (40) and a single second reactor (48), configured in order to be fed sequentially either by the second system (46) for feeding with reaction stream or by the system (49) for feeding with regeneration stream; and which, preferably, is configured so that one and the same regeneration stream resulting from the system (49) for feeding with regeneration stream passes successively into the first reactor (40) and then the second reactor (48) or passes successively into the second reactor (48) and then the first reactor (40).

33. A composition comprising tetrafluoropropene and containing, in molar proportions:
less than 100 ppm of chloromethane; and/or
less than 100 ppm of 1,1-difluoroethane; and/or
less than 100 ppm of fluoromethane; and/or
less than 100 ppm of difluoromethane.

34. The composition as in embodiment 33, in which the tetrafluoropropene is 2,3,3,3-tetrafluoropropene.

35. The composition as in embodiment 33 or 34, containing, in molar proportions:
less than 50 ppm of chloromethane; and/or
less than 50 ppm of 1,1-difluoroethane; and/or
less than 50 ppm of fluoromethane; and/or
less than 50 ppm of difluoromethane.

The invention claimed is:

1. A plant for the manufacture of a tetrafluoropropene, comprising a first gas-phase catalytic fluorination reactor comprising a bed of fluorination catalyst, said first gas-phase catalytic fluorination reactor being configured to be fed by two alternating systems, the alternating systems comprising:
a first system for feeding with reaction stream comprising a chlorinated compound and hydrofluoric acid, the proportion of oxygen optionally present in this reaction stream being less than 0.05 mol % with respect to the chlorinated compound; and
a second system for feeding with regeneration stream comprising an oxidizing agent, the plant further comprising:
a second catalytic fluorination reactor;
a system for collecting a stream of products connected at the outlet of the first catalytic fluorination reactor;
a separation unit fed by the system for collecting a stream of products;
a first collecting pipe and a second collecting pipe which are connected at the outlet of the separation unit, the first collecting pipe being configured to transport a stream comprising hydrochloric acid and the tetrafluoropropene and the second collecting pipe being configured to transport a stream comprising hydrofluoric acid and chlorinated compound;
an intermediate collecting system connected at the outlet of the second reactor;
a third system for feeding with reaction medium configured to feed the first catalytic fluorination reactor, this being itself fed by the intermediate collecting system and by the first system for feeding with reaction stream;
a fourth system for feeding with reaction medium configured to feed the second catalytic fluorination reactor, this being itself fed by the second collecting pipe; and
a system for collecting a stream of gases stream resulting from the regeneration,
wherein the bed of fluorination catalyst comprises a bulk Cr-based catalyst,
wherein the second system for feeding with regeneration stream is configured to feed the first reactor and/or the second reactor.

2. The plant as claimed in claim 1, in which the reaction stream is essentially devoid of oxygen.

3. The plant as claimed in claim 1, in which the regeneration stream contains at least 1 mol % of oxygen with respect to the total regeneration stream.

4. The plant as claimed in claim 1, wherein the plant further comprises additional catalytic fluorination reactors each being configured to be fed by the two alternating systems.

5. The plant as claimed in claim 4, configured so that, when one of the reactors is fed by the first system for feeding with reaction stream, another reactor is fed by the second system for feeding with regeneration stream.

6. The plant as claimed in claim 1, configured so that:
the first system for feeding with reaction stream feeds the first catalytic fluorination reactor at the bottom and the second system for feeding with regeneration stream feeds the first catalytic fluorination reactor at the bottom; or
the first system for feeding with reaction stream feeds the first catalytic fluorination reactor at the bottom and the second system for feeding with regeneration stream feeds the first catalytic fluorination reactor at the top; or
the first system for feeding with reaction stream feeds the first catalytic fluorination reactor at the top and the second system for feeding with regeneration stream feeds the first catalytic fluorination reactor at the bottom; or
the first system for feeding with reaction stream feeds the first catalytic fluorination reactor at the top and the second system for feeding with regeneration stream feeds the first catalytic fluorination reactor at the top.

7. The plant as claimed in claim 1, in which:
the tetrafluoropropene is 2,3,3,3-tetrafluoropropene; or
the tetrafluoropropene is 1,3,3,3-tetrafluoropropene.

8. The plant as claimed in claim 1, in which the chlorinated compound is chosen from tetrachloropropenes, chlorotrifluoropropenes, pentachloropropanes and mixtures of these.

9. The plant as claimed in claim 1, the plant further comprising:
at least one unit for the manufacture of the chlorinated compound; configured to be fed by:
a fifth system for feeding with reaction medium comprising a preliminary compound and hydrofluoric acid, the proportion of oxygen optionally present in this reaction stream being less than 0.05 mol % with respect to the preliminary compound.

10. The plant as claimed in claim 9, wherein the unit for the manufacture of the chlorinated compound is a preliminary fluorination reactor that is also configured to be fed by the second system for feeding with regeneration stream comprising an oxidizing agent.

11. The plant as claimed in claim 9, in which the preliminary compound is 1,1,1,2,3-pentachloropropane and/or 1,1,2,2,3-pentachloropropane, the chlorinated compound is 1 chloro-3,3,3-trifluoropropene and the tetrafluoropropene is 2,3,3,3-tetrafluoropropene.

12. The plant as claimed in claim 1, which further comprises an additional reactor, wherein at least two of the reactors are configured so that, when one of them is fed by the fourth system for feeding with reaction medium, the other reactor is fed by the second system for feeding with regeneration stream.

13. The plant as claimed in claim 1, further comprising at least two additional reactors configured so that, when the additional reactors are respectively fed by the third system for feeding with reaction medium and the fourth system for feeding with reaction medium, the first catalytic fluorination reactor and the second catalytic fluorination reactor are fed by the second system for feeding with regeneration stream.

14. The plant as claimed in claim 1, wherein the second catalytic fluorination reactor is configured to be fed sequentially either by the fourth system for feeding with reaction medium or by the second system for feeding with regeneration stream.

15. The plant as claimed in claim 1, wherein the first catalytic fluorination reactor and the second catalytic fluorination reactor are configured to be fed sequentially either by the fourth system for feeding with reaction medium or by the second system for feeding with regeneration stream.

16. The plant as claimed in claim 1, wherein the bed of fluorination catalyst is a mixed catalyst comprising Cr and at least one element selected from Mg and Zn, the atomic ratio of Mg/Cr or Zn/Cr being 0.1 to 5.0.

17. The plant as claimed in claim 1, wherein the first and second catalytic fluorination reactors, the intermediate collecting system connected at the outlet of the second catalytic fluorination reactor, and the second system for feeding with regeneration stream are configured such that when the second system for feeding with regeneration stream feeds the second catalytic fluorination reactor, the first system for feeding with reaction medium simultaneously feeds the first catalytic fluorination reactor,
   wherein the plant is configured such that a reaction between a chlorinated compound and hydrofluoric acid is carried out in the first reactor simultaneously with a regeneration of the fluorination catalyst in the second catalytic fluorination reactor.

18. The plant as claimed in claim 1, further comprising an additional catalytic fluorination reactor, wherein:
   a first system of valves is at the inlets of the second and additional catalytic fluorination reactors and a second system of valves is at the outlets of these two catalytic fluorination reactors,
   wherein the plant is configured such that a reaction between a chlorinated compound and hydrofluoric acid is carried out in the first catalytic fluorination reactor simultaneously with a regeneration of the fluorination catalyst in the second catalytic fluorination reactor;
   wherein the second and additional catalytic fluorination reactors are configured to operate alternately in a fluorination mode and in a regeneration mode and, by controlling the first and second systems of valves, the plant is arranged to operate in either of two phases;
   wherein, in a first phase, the second catalytic fluorination reactor operates in the fluorination mode by being fed by the fourth system for feeding with reaction medium and feeds the intermediate collecting system, while the additional catalytic fluorination reactor operates in the regeneration mode by being fed by the second system for feeding with regeneration stream and feeds the system for collecting a stream of gases resulting from the regeneration;
   wherein, in a second phase, the second and additional catalytic fluorination reactors operate in a configuration opposite the configuration of the first phase.

19. The plant as claimed in claim 1, wherein the separation unit is a distillation unit.

* * * * *